United States Patent
Williams et al.

(10) Patent No.: US 10,702,302 B2
(45) Date of Patent: Jul. 7, 2020

(54) ADAPTER ASSEMBLY INCLUDING A REMOVABLE TROCAR ASSEMBLY

(71) Applicant: Covidien LP, Mansfield, MA (US)

(72) Inventors: Justin Williams, Southbury, CT (US); David Valentine, East Hampton, CT (US); Stephen Paul, East Hartford, CT (US)

(73) Assignee: Covidien LP, Mansfield, MA (US)

( * ) Notice: Subject to any disclaimer, the term of this patent is extended or adjusted under 35 U.S.C. 154(b) by 440 days.

(21) Appl. No.: 15/157,136

(22) Filed: May 17, 2016

(65) Prior Publication Data

US 2017/0333077 A1 Nov. 23, 2017

(51) Int. Cl.
| | |
|---|---|
| A61B 17/34 | (2006.01) |
| A61B 17/115 | (2006.01) |
| A61B 17/072 | (2006.01) |
| A61B 17/00 | (2006.01) |
| A61B 90/00 | (2016.01) |

(52) U.S. Cl.
CPC ........ *A61B 17/34* (2013.01); *A61B 17/07207* (2013.01); *A61B 17/1155* (2013.01); *A61B 2017/0046* (2013.01); *A61B 2017/00473* (2013.01); *A61B 2017/00477* (2013.01); *A61B 2017/07257* (2013.01); *A61B 2017/347* (2013.01); *A61B 2090/0813* (2016.02)

(58) Field of Classification Search
CPC .......... A61B 17/07207; A61B 17/1155; A61B 17/34; A61B 2017/347; A61B 2017/00477; A61B 2017/0473; A61B 2017/0046
See application file for complete search history.

(56) References Cited

U.S. PATENT DOCUMENTS

| | | | |
|---|---|---|---|
| 2,777,340 A | 1/1957 | Hettwer et al. |
| 2,957,353 A | 10/1960 | Babacz |
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |

(Continued)

FOREIGN PATENT DOCUMENTS

| | | |
|---|---|---|
| CA | 2451558 A1 | 1/2003 |
| CN | 1547454 A | 11/2004 |

(Continued)

OTHER PUBLICATIONS

Extended European Search Report dated Feb. 20, 2018, issued in EP Appln. No. 17171265.

(Continued)

*Primary Examiner* — Julie A Szpira
(74) *Attorney, Agent, or Firm* — Carter, DeLuca & Farrell LLP

(57) ABSTRACT

An adapter assembly for connecting a surgical loading unit to a handle assembly is provided. The adapter assembly includes a sleeve, a trocar assembly releasably securable within the sleeve, and a locking mechanism configured to releasably secure the trocar assembly within the sleeve.

19 Claims, 15 Drawing Sheets

(56) References Cited

U.S. PATENT DOCUMENTS

| | | |
|---|---|---|
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |

(56) References Cited

U.S. PATENT DOCUMENTS

| | | |
|---|---|---|
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Zemlok et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2005/0261698 A1* | 11/2005 | Powell .............. A61B 17/1615 606/96 |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |

(56) References Cited

U.S. PATENT DOCUMENTS

| | | |
|---|---|---|
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0042206 A1* | 2/2014 | Milliman ............ A61B 17/068 227/175.2 |
| 2014/0110455 A1 | 4/2014 | Ingmanson et al. |
| 2014/0166717 A1* | 6/2014 | Swayze ............. A61B 17/1155 227/4 |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0129636 A1* | 5/2015 | Mulreed ............. A61B 17/115 227/177.1 |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 1957854 A | 5/2007 |
| CN | 101495046 A | 7/2009 |
| CN | 102247182 A | 11/2011 |
| DE | 102008053842 A1 | 5/2010 |
| EP | 0705571 A1 | 4/1996 |
| EP | 1563793 A1 | 8/2005 |
| EP | 1769754 A1 | 4/2007 |
| EP | 2316345 A1 | 5/2011 |
| EP | 2668910 A2 | 12/2013 |
| EP | 2873380 A1 | 5/2015 |
| ES | 2333509 A1 | 2/2010 |
| JP | 2005-125075 A | 5/2005 |
| KR | 20120022521 A | 3/2012 |

(56) References Cited

FOREIGN PATENT DOCUMENTS

| WO | 2005037084 A2 | 4/2005 |
|---|---|---|
| WO | 2011/108840 A2 | 9/2011 |
| WO | 2012/040984 A1 | 4/2012 |

OTHER PUBLICATIONS

Extended European Search Report corresponding to counterpart International Application No. EP 14 18 4882.0 dated May 12, 2015.
Canadian Office Action corresponding to counterpart International Application No. CA 2640399 dated May 7, 2015.
Japanese Office Action corresponding to counterpart International Application No. JP 2011-197365 dated Mar. 23, 2015.
Japanese Office Action corresponding to counterpart International Application No. JP 2011-084092 dated May 20, 2015.
Japanese Office Action corresponding to counterpart International Application No. JP 2014-148482 dated Jun. 2, 2015.
Extended European Search Report corresponding to counterpart International Application No. EP 14 18 9358.6 dated Jul. 8, 2015.
Extended European Search Report corresponding to counterpart International Application No. EP 14 19 6148.2 dated Apr. 23, 2015.
Partial European Search Report corresponding to counterpart International Application No. EP 14 19 6704.2 dated May 11, 2015.
Australian Office Action corresponding to counterpart International Application No. AU 2010241367 dated Aug. 20, 2015.
Partial European Search Report corresponding to counterpart International Application No. EP 14 19 9783.3 dated Sep. 3, 2015.
Extended European Search Report corresponding to counterpart International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015
Extended European Search Report corresponding to International Application No. EP 15 19 0760.9 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2013101559718; 23 total pages.

* cited by examiner

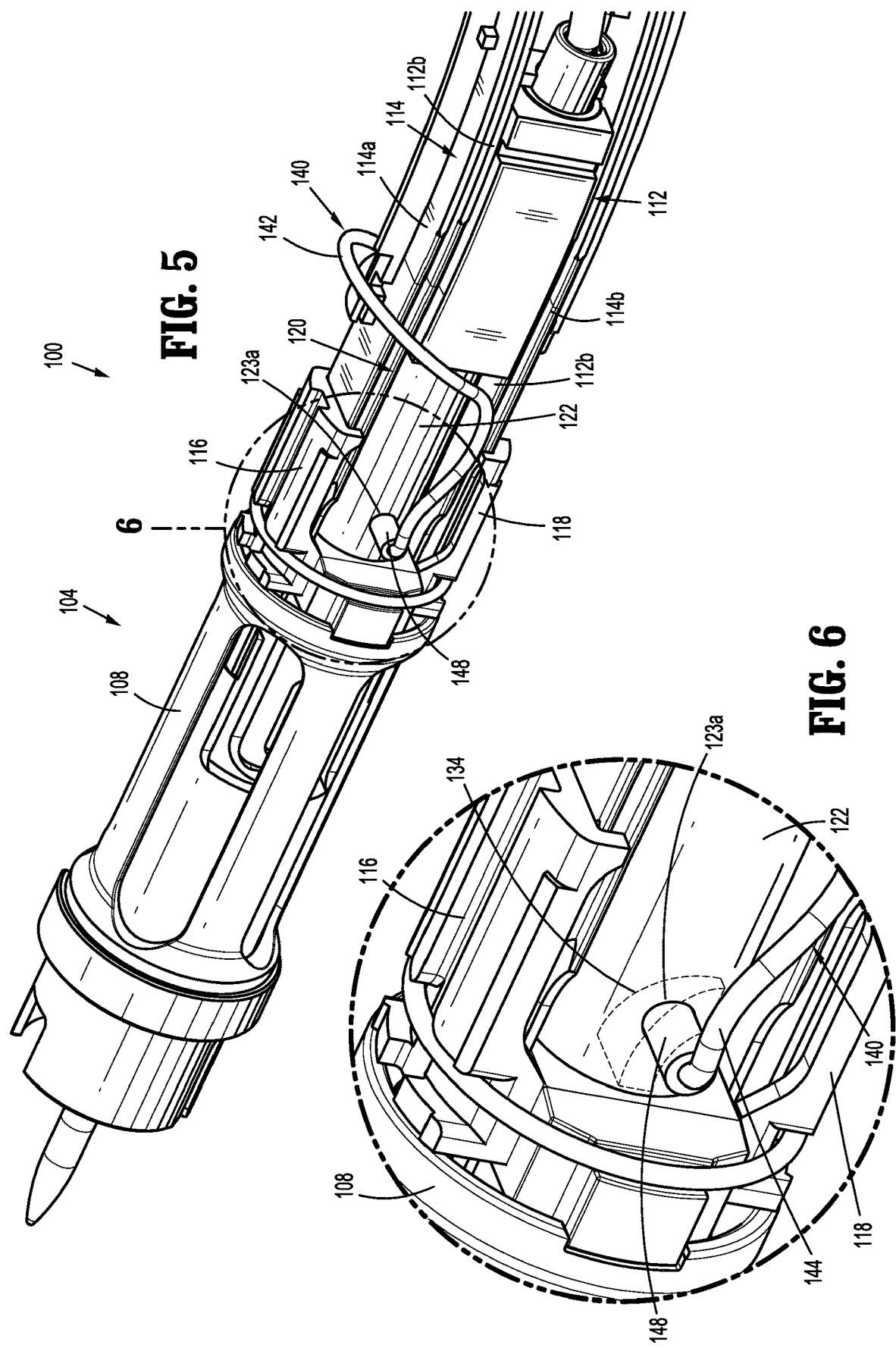

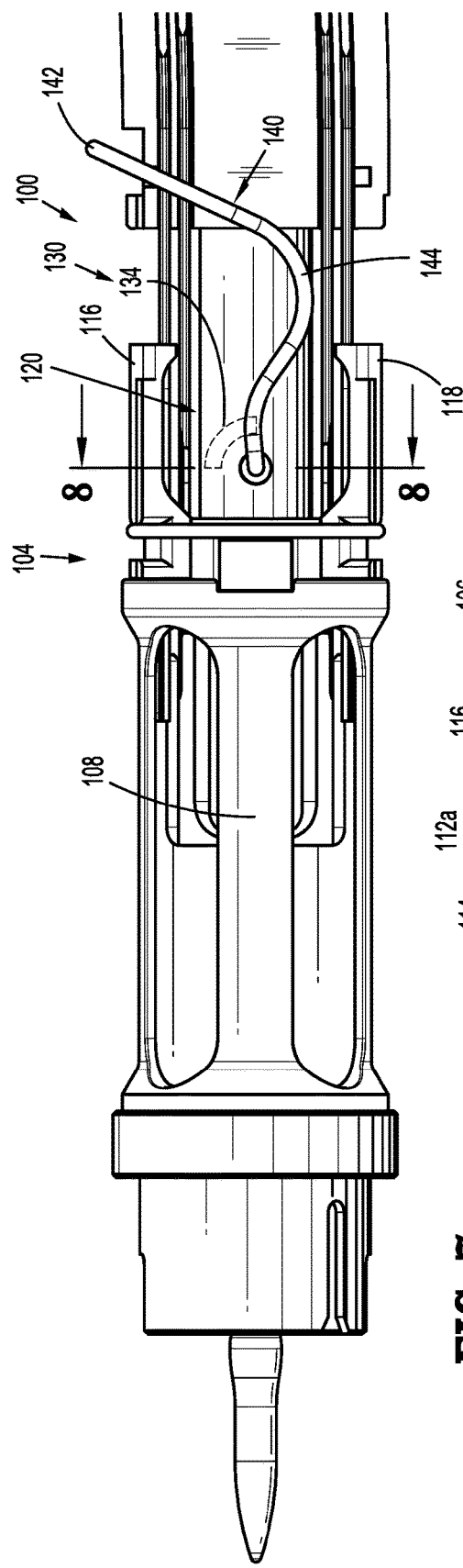
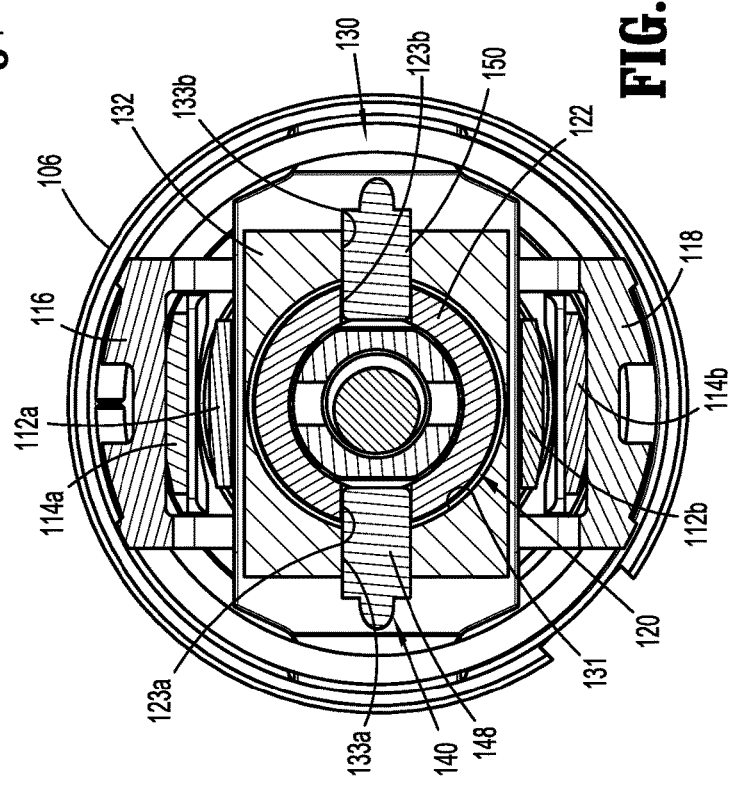
FIG. 7
FIG. 8

ADAPTER ASSEMBLY INCLUDING A REMOVABLE TROCAR ASSEMBLY

BACKGROUND

Technical Field

The present disclosure relates to reusable surgical stapling devices having removable trocar assemblies for use with circular staplers. More particularly, the present disclosure relates to reusable adapter assemblies including locking mechanisms for releasably securing the removable trocar assemblies to a handle assembly of a surgical stapling device.

Background of Related Art

Surgical devices for applying staples, clips, or other fasteners to tissue are well known. Typically, endoscopic stapling devices include an actuation unit, i.e., a handle assembly for actuating the device and a shaft for endoscopic access, and a tool assembly disposed at a distal end of the shaft. In certain of these devices, the shaft includes an adapter assembly, having a proximal end securable to the handle assembly and a distal end securable to the tool assembly.

The adapter assembly may be reusable and may include a trocar assembly. To facilitate sterilization and cleaning of the adapter assembly, it would be beneficial to have a locking mechanism for releasably securing the removable trocar assembly within the adapter assembly.

SUMMARY

An adapter assembly for connecting a surgical loading unit to a handle assembly is provided. The adapter assembly including a sleeve, a trocar assembly releasably securable within the sleeve, and a locking mechanism configured to releasably secure the trocar assembly within the sleeve. The trocar assembly includes a trocar housing defining first and second locking slots. The locking mechanism includes a retaining member having first and second engagement portions configured for selective reception within the first and second locking slots, respectively, of the trocar housing.

In embodiments, the retainer member is a formed wire and the first and second engagement portions include first and second locking posts movable between a first position engaged with the trocar assembly such that the trocar assembly is securely received within the sleeve, and a second position disengaged from the trocar assembly such that the trocar assembly is removable from within the sleeve. The retainer member may be configured to be pivoted between the first position and the second position.

The locking mechanism may further include a lock housing, and first and second ramp members extending from the lock housing. The first and second ramp members may be configured to urge the first and second locking posts from an initial position in engagement with the trocar housing to a spaced apart position disengaged from the trocar housing as the retainer member is moved from the first position to the second position. The retainer member may include a base portion. The first and second leg portions may extend from the base portion. The first and second engagement portions may extend from the respective first and second leg portions.

The adapter assembly may further include upper and lower band guides. The retainer member may be slidably received over the upper band guide and engages the lower band guide. Engagement of the retainer member with the lower band guide may bias the retainer member radially outwardly. The retainer member may be movable relative to the upper and lower band guides from a first position in engagement with the trocar housing, to a second position disengaged from the trocar housing. The base portion of the retainer member may be configured to move radially inward relative to the sleeve. The retainer member may further include first and second posts for maintaining the retainer member about the upper band guide.

The first and second engagement portions may include first and second tabs for engaging the trocar housing of the trocar assembly. The first and second engagement portions may be curved towards one another and may be configured to engage the trocar housing of the trocar assembly.

Also provided is an adapter assembly for connecting a loading unit to a handle assembly. The adapter assembly including a sleeve, upper and lower band guides disposed within the sleeve, a trocar assembly releasably securable within the sleeve, and a locking mechanism configured to releasably secure the trocar assembly within the sleeve. The trocar assembly includes a trocar housing defining at least a first retention slot. The locking mechanism includes a retaining member pivotally secured to the lower band guide. The retainer member includes a protrusion configured for selective reception within the at least first retention slot of the trocar housing.

In embodiments, the retainer member is movable between a first position engaged with the trocar housing and a second position disengaged from the trocar housing. The locking mechanism may include a latch member having an engagement portion for facilitating movement of the latch member by a user. The locking mechanism may further include a spring for biasing the latch member to a locked position. The latch member may include a locking portion for engaging the upper band guide when the retainer member is in the first position.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein:

FIG. 5 is a rear perspective view of the distal end of the adapter assembly shown in FIGS. 1-3, with the outer sleeve removed therefrom and with a locking mechanism in a locked position;

FIG. 6 is an enlarged view of the indicated are of detail in FIG. 6;

FIG. 7 is a side view of the distal end of the adapter assembly shown in FIGS. 1-3, with the outer sleeve removed therefrom and with the locking mechanism in the locked position;

FIG. 8 is a cross-sectional end view taken along section line 8-8 shown in FIG. 7;

DETAILED DESCRIPTION

Figure 1:
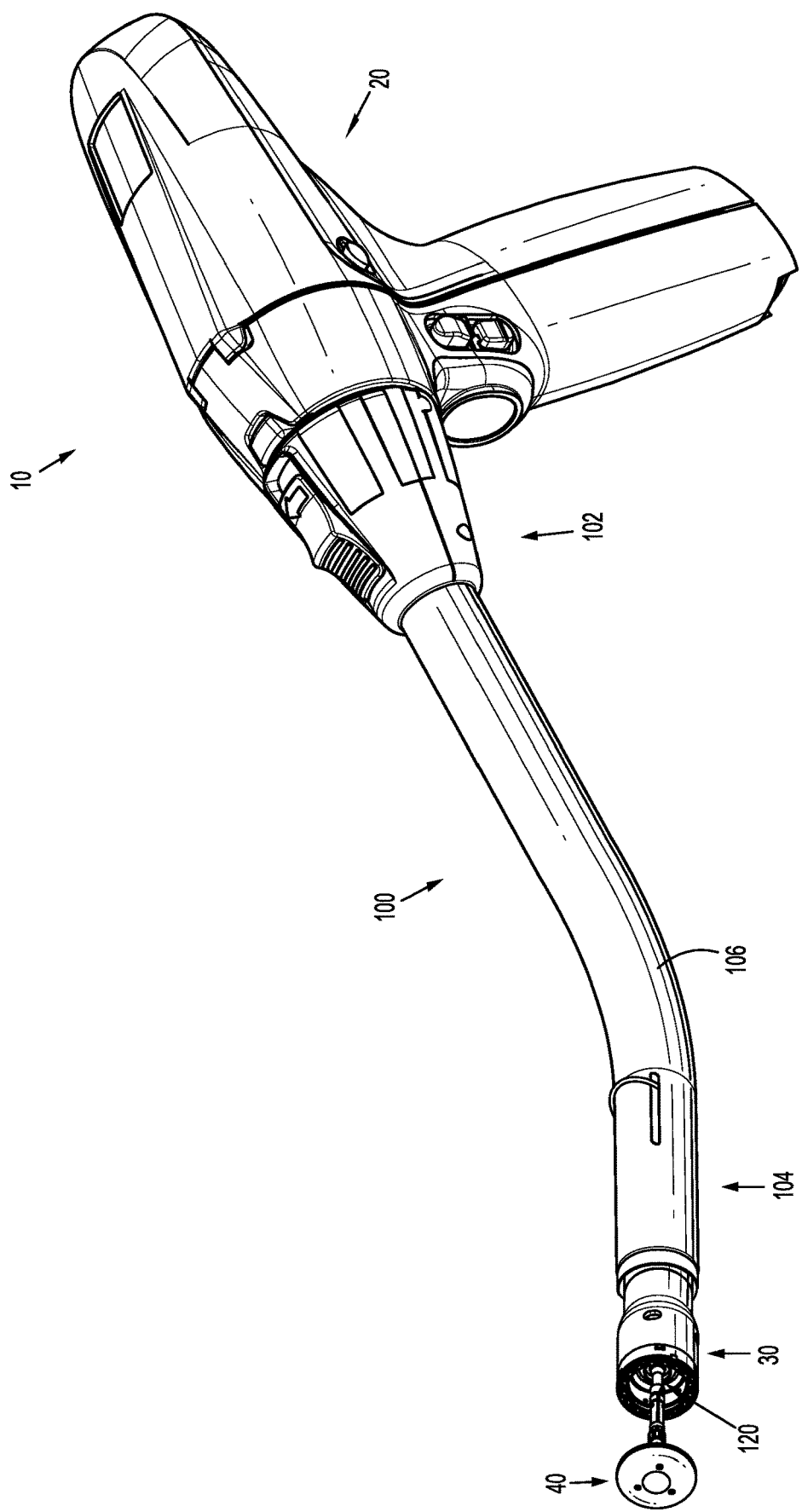
FIG. 1 is a perspective view of a surgical stapling device including an handle assembly with an adapter assembly according to one embodiment of the present disclosure.

Embodiments of the presently disclosed adapter assembly including a removable trocar assembly will now be described in detail with reference to the drawings in which like reference numerals designate identical or corresponding elements in each of the several views. As is common in the art, the term "proximal" refers to that part or component closer to the user or operator, i.e. surgeon or clinician, while the term "distal" refers to that part or component further away from the user.

Referring initially to FIG. 1, an adapter assembly according to an embodiment of the present disclosure, shown generally as adapter assembly 100, is a component of an electromechanical surgical stapling device 10. The surgical stapling device 10 further includes a powered handle assembly 20, a loading unit 30, and an anvil assembly 40. Although shown and described with reference to the electromechanical surgical stapling device 10, the aspects of the present disclosure may be modified for use with manual surgical stapling devices having various configurations, and with powered surgical stapling devices having alternative configurations. For a detailed description of an exemplary powered handle assembly, please refer to commonly owned U.S. Pat. No. 9,023,014 ("the '014 patent") and U.S. Pat. No 9,055,943 ("the '943 patent"), the content of each of which is incorporated by reference herein in its entirety.

With continued reference to FIG. 1, the adapter assembly 100 includes a proximal portion 102 configured for operable connection to the handle assembly 20, and a distal portion 104 configured for operable connection to the loading unit 30 and for releasable attachment of a trocar assembly 120 to which the anvil assembly 40 is secured. Although shown and described as forming an integral unit, it is envisioned that the proximal and distal portions 102, 104 may be formed as separate units that are releasably or fixedly securable to one another.

The adapter assembly 100 will only be described to the extent necessary to fully disclose the aspects of the present disclosure. For a detailed description of an exemplary adapter assembly, please refer to commonly owned U.S. patent application Ser. No. 14/875,766 ("the '766 application"), filed Oct. 6, 2015, the content of which is incorporated by reference herein in its entirety.

Figure 2:
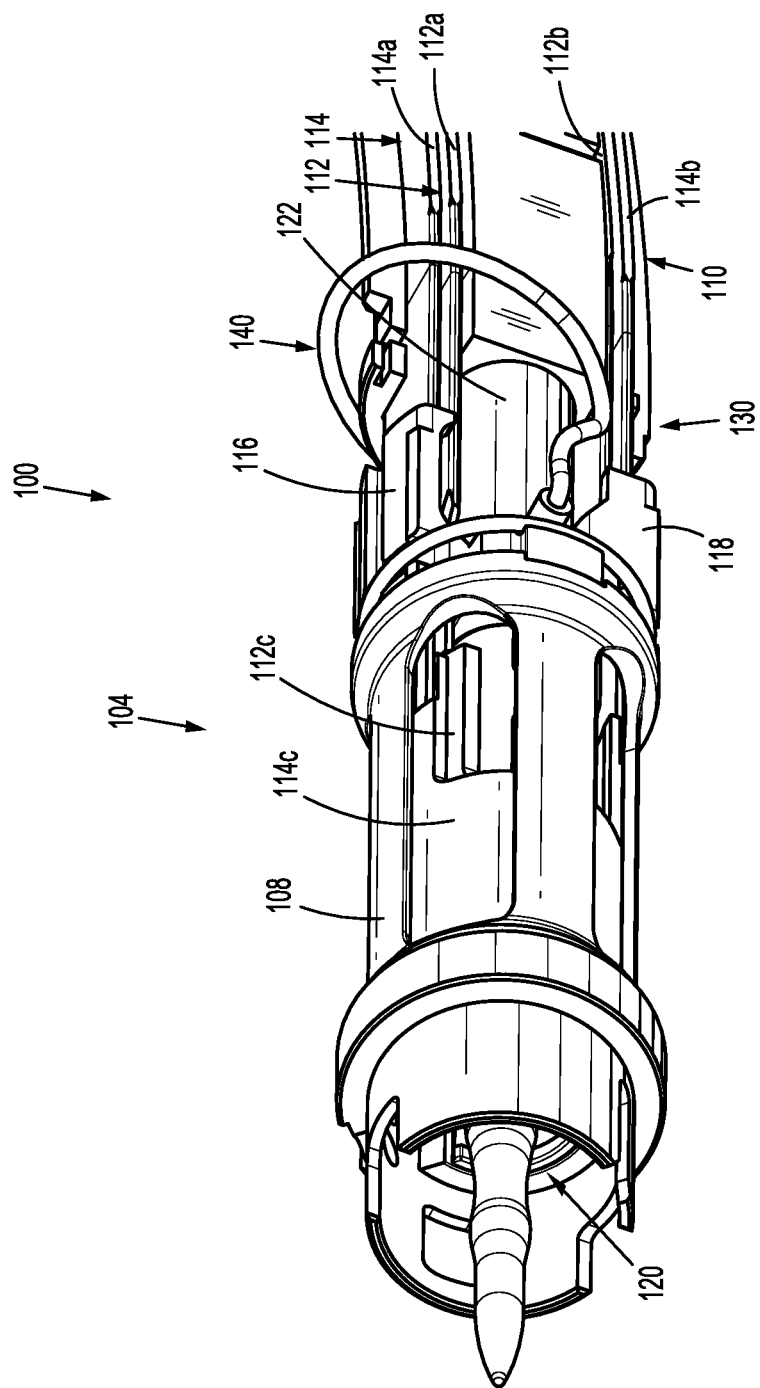
FIG. 2 is a perspective view of a distal end of the adapter assembly shown in FIG. 1 with an outer sleeve removed therefrom.

With additional reference to FIG. 2, the adapter assembly 100 includes an outer sleeve 106 (FIG. 1), and a connector housing 108 secured within a distal end of the outer sleeve 106. The connector housing 108 is configured to releasably secure an end effector, e.g., the loading unit 30 (FIG. 1), to the adapter assembly 100.

With continued reference to FIG. 2, the adapter assembly 100 includes a drive assembly 110 that extends through the outer sleeve 106 (FIG. 1) and that includes an inner flexible band assembly 112 and an outer flexible band assembly 114. The inner flexible band assembly 112 includes first and second inner flexible bands 112a, 112b, and an inner pusher member 112c connected to the distal ends of the first and second inner flexible bands 112a, 112b. Similarly, the outer flexible band assembly 114 includes first and second outer flexible bands 114a, 114b, and an outer pusher member 114c connected to the distal ends of the first and second outer flexible bands 114a, 114b. The first inner and outer flexible bands 112a, 114a of the respective inner and outer flexible band assemblies 112, 114 are supported by an upper band guide 116, and the second inner and outer flexible bands 112b, 114b of the respective inner and outer flexible band assemblies 112, 114 are supported by a lower band guide 118. For a detailed description of the structure and function of an exemplary drive assembly, please refer to the '766 application, the content of which was previously incorporated herein by reference in its entirety.

Figure 3:
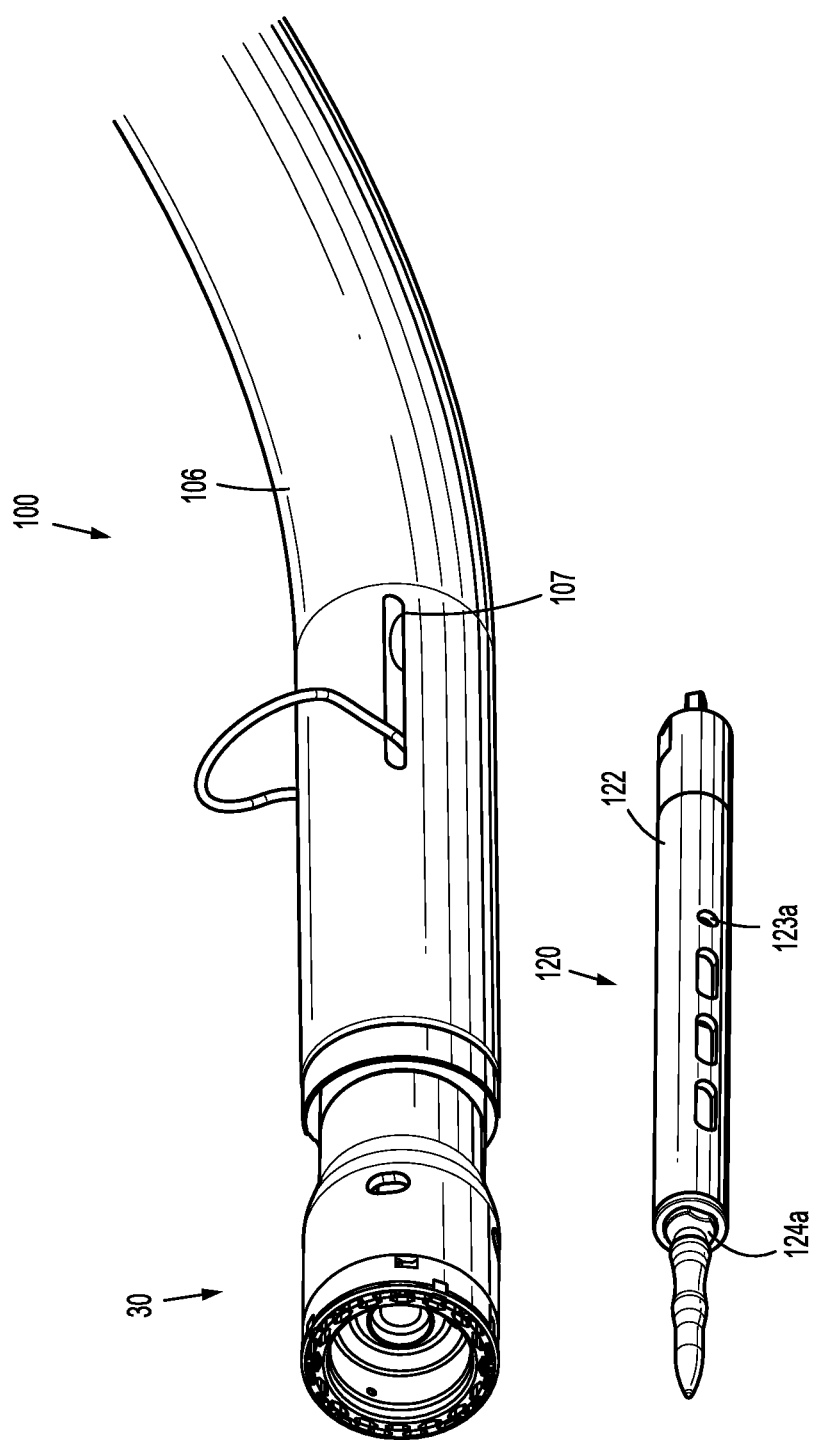
FIG. 3 is a front perspective view of the distal end of the adapter assembly shown in FIG. 1, including a loading unit secured to the adapter assembly and a trocar assembly separate from the adapter assembly.

With additional reference to FIG. 3, the adapter assembly 100 is configured to receive the trocar assembly 120 within the connector housing 108 (FIG. 2) thereof, and includes a locking mechanism 130 (FIG. 2) for releasably securing the trocar assembly 120 relative to and within the connector housing 108 of the adapter assembly 100.

Figure 4:
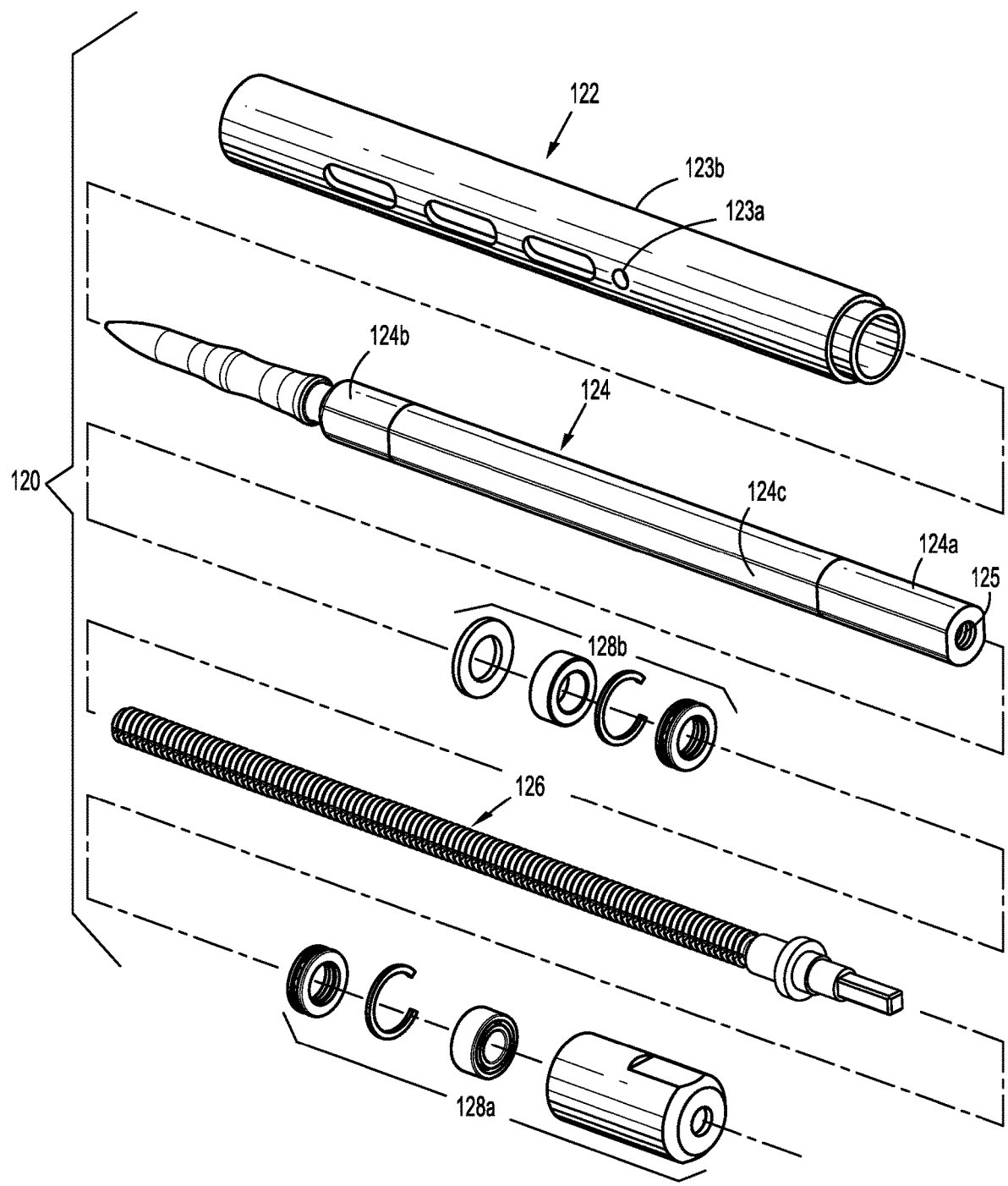
FIG. 4 is a perspective view of the removable trocar assembly shown in FIG. 4, with parts separated.

With reference now to FIG. 4, the trocar assembly 120 of the adapter assembly 100 (FIG. 2) includes an outer housing 122 defining a lumen 122a therein, a trocar member 124 slidably disposed within the lumen 122a of the outer housing 122, and a drive screw 126 operably received within the trocar member 124 for axially moving the trocar member 124 relative to the outer housing 122. More specifically, a proximal end 124a of the trocar member 124 defines a threaded bore 125 which is dimensioned to receive the drive screw 126. The outer-surface of the drive screw 126 is threaded such that rotation of the drive screw 126 causes longitudinal movement of the trocar member 124 within the outer housing 122 of the trocar assembly 120. The trocar member 124 is keyed within the outer housing 122 such that the trocar member 124 does not rotate relative to the outer housing 122 when the drive screw 126 is rotated. For example, as shown in FIG. 4, the trocar member 124 includes a flattened surface 124c for engaging a surface (not shown) of the outer housing 122 to rotationally fix the trocar member 124 relative to the outer housing 122. A distal end 124b of trocar member 124 is configured to releasably engage an anvil assembly, e.g., the anvil assembly 40 (FIG. 1).

Proximal and distal bearing assemblies 128a, 128b are mounted within a proximal end of outer housing 122 of trocar assembly 120 for rotatably supporting the drive screw 126 within the outer housing 122 and the trocar member 124. As will be described in further detail below, the outer housing 122 defines first and second apertures 123a, 123b (FIG. 8) for receiving the respective first and second locking ends 148, 150 (FIG. 7) of the retaining member 140 of the locking mechanism 130 of the adapter assembly 100.

With reference now to FIGS. 5-11, the locking mechanism 130 of the adapter assembly 100 includes a housing 132 (FIG. 8) through which the trocar assembly 120 is received, and a retainer member 140 for securing the trocar assembly 120 relative to the housing 132. As seen in FIG. 8, the housing 132 of the locking mechanism 130 is received between the first and second band guides 116, 118. As will be described in further detail below, the retainer member 140 is movable between a locked position (FIGS. 7 and 8) in which the retainer member 140 engages the trocar assembly 120 to secure the trocar assembly 120 relative to the housing 132, and a unlocked position (FIGS. 10 and 11) in which the retainer member 140 is disengaged from the trocar assembly 120 such that the trocar assembly 120 may be removed from within the housing 132 of the locking mechanism 130.

With particular reference to FIG. 8, the housing 132 of the locking mechanism 130 is supported within the outer sleeve 106 of the adapter assembly 100 and defines a throughbore 131 through which the trocar assembly 120 is received. The housing 132 further defines first and second openings 133a, 133b extending outwardly from the throughbore 131. As will be described in further detail below, the first and second openings 133a, 133b of the housing 132 are configured to align with the first and second apertures 123a, 123b in the outer housing 122 of the trocar assembly 120 when the trocar assembly 120 is received within the throughbore 131 of the housing 132.

Figure 9:
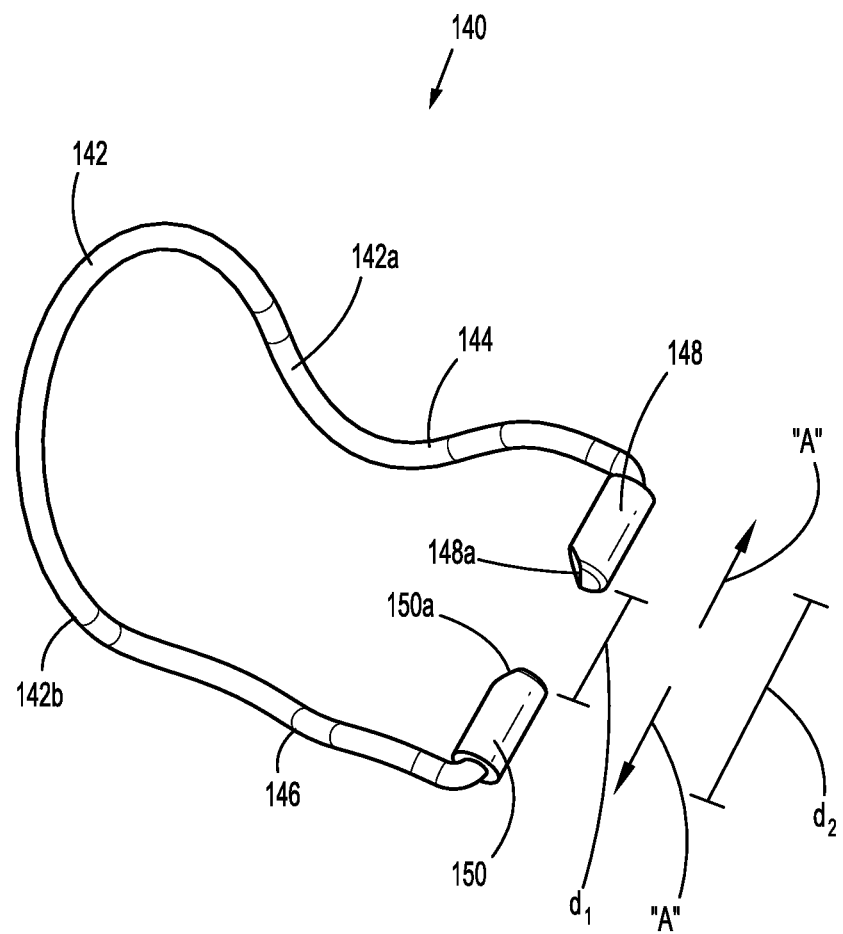
FIG. 9 is a perspective side view of a retainer member of the locking mechanism shown in FIG. 5.

With additional reference to FIG. 9, the retainer member 140 of the locking mechanism 130 includes a wire form curved body portion 142, curved first and second leg portions 144, 146 extending outwardly from the curved body portion 142, and first and second locking posts 148, 150 extending inwardly from the respective first and second leg portions 144, 146. When the retainer member 140 is secured to the housing 132, the curved body portion 142 of the retainer member 140 is received through a pair of slots 107 (FIG. 3, only one visible) in the outer sleeve 106 of the adapter assembly 100 and is configured to be selectively received about the drive assembly 110 and the trocar assembly 120 to secure the trocar assembly 120 relative to housing 132 of the locking mechanism 130.

In operation, the ends 142a, 142b (FIG. 9) of the curved body portion 142 of the retainer member 140 and/or the first and second leg portions 144, 146 of the retainer member 140 flex outwardly as the retainer member 140 is moved from the unlocked position (FIG. 10) to the locked position (FIG. 7). Additionally, when the retainer member 140 is in the locked position, the ends 142a, 142b of the curved body portion 142 and/or the first and second leg portions 144, 146 return to an unflexed condition about the housing 132 of the locking mechanism 130 to secure the retainer member 140 in the locked position.

Figures 10, 11:
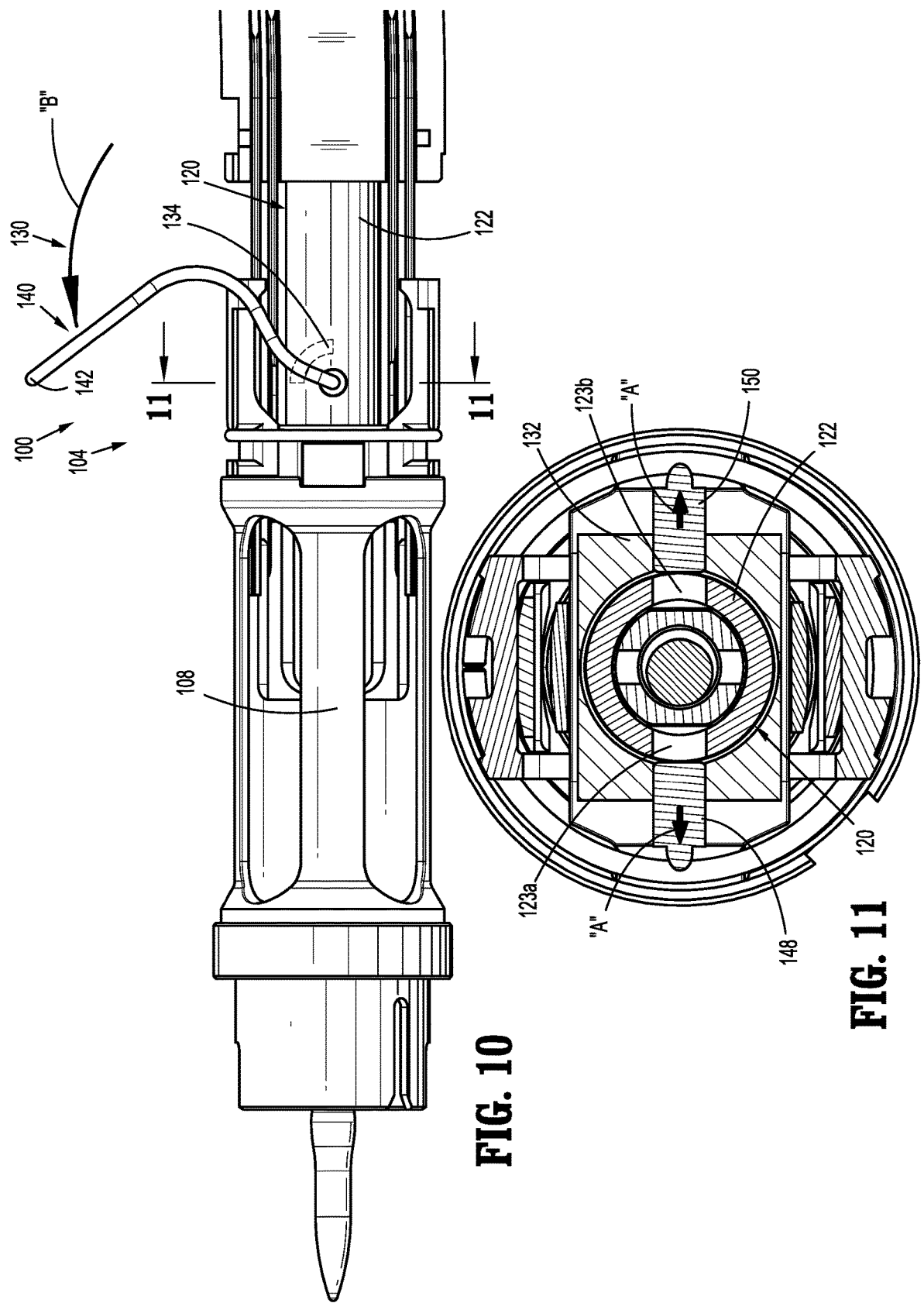
FIG. 10 is a side view of the distal end of the adapter assembly shown in FIGS. 1-3, with the outer sleeve removed and the locking mechanism in an unlocked position.
FIG. 11 is a cross-sectional end view taken along section line 11-11 shown in FIG. 10.
Figure 12:
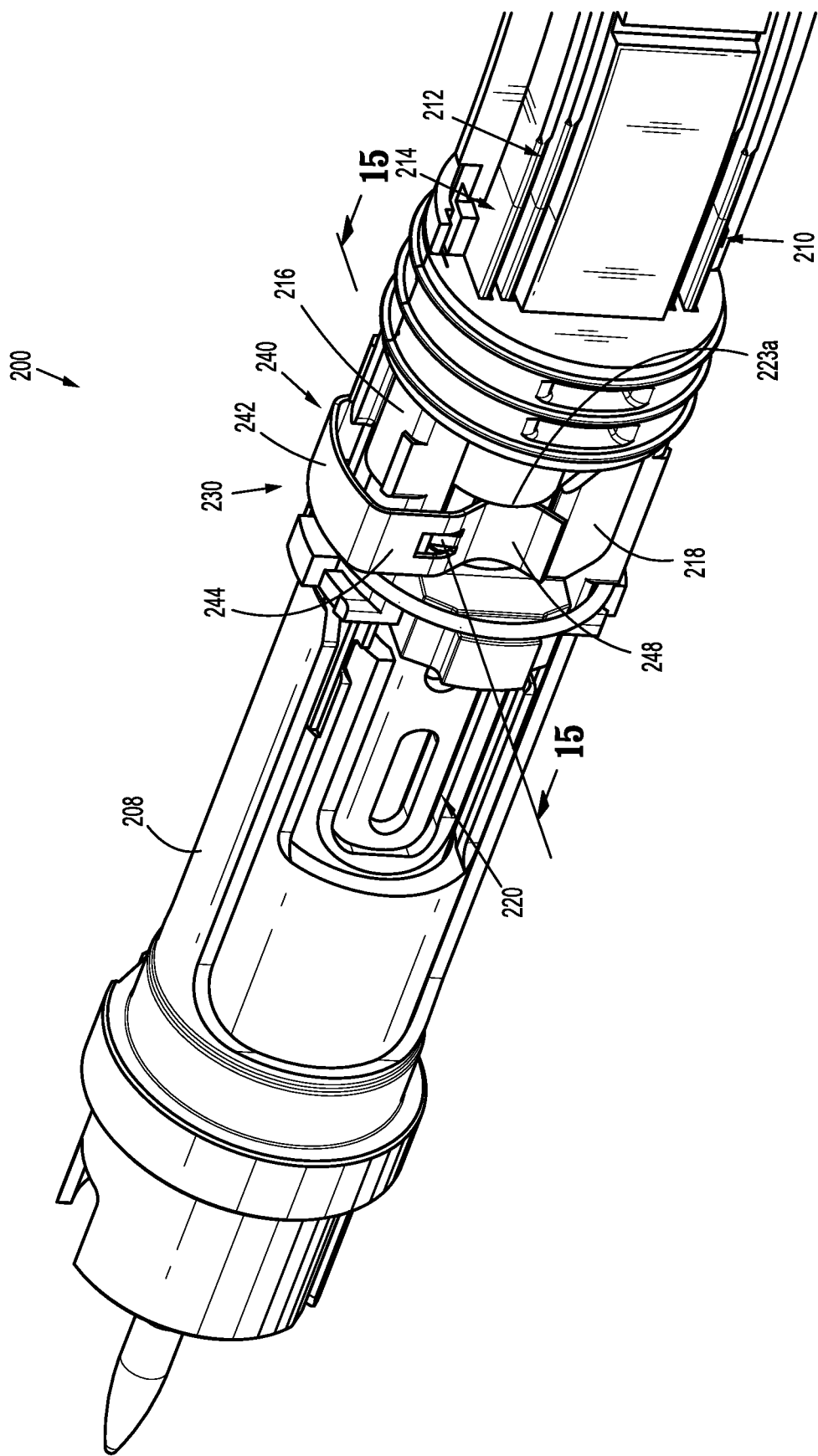
FIG. 12 is a rear, perspective view of a distal end of an adapter assembly according to another embodiment of the present disclosure with an outer sleeve removed.
Figure 13:
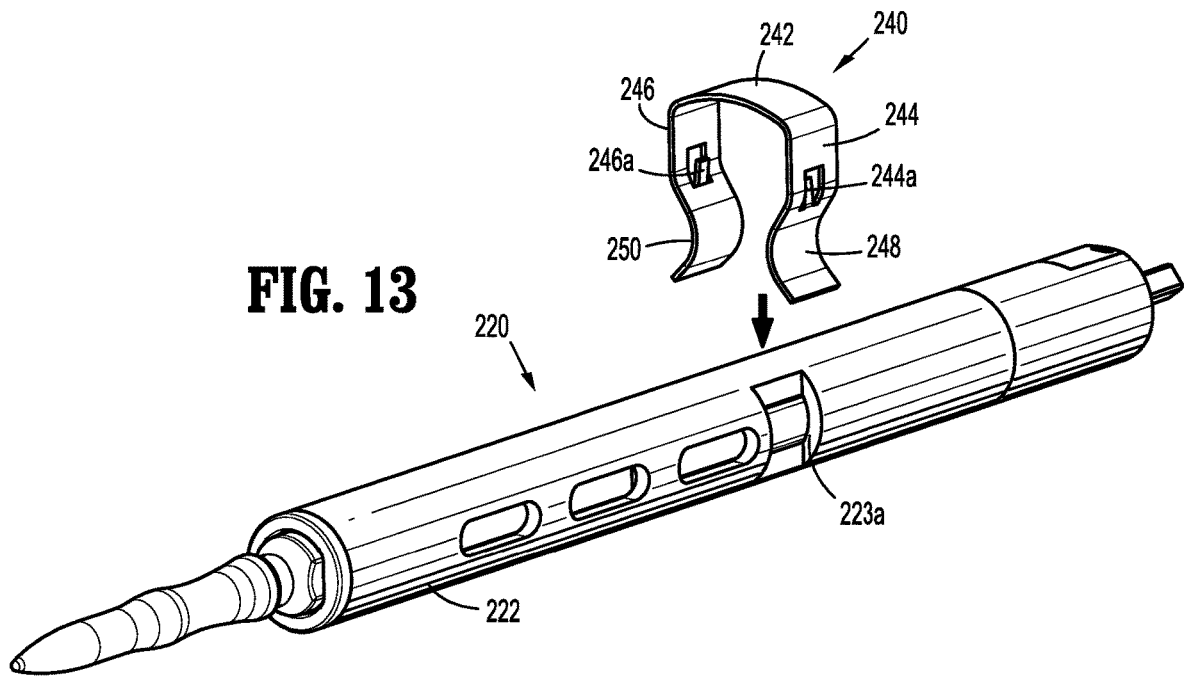
FIG. 13 is a front, perspective view of a removable trocar assembly and a retainer member of a locking mechanism of the adapter assembly shown in FIG. 12, separated.
Figure 14:
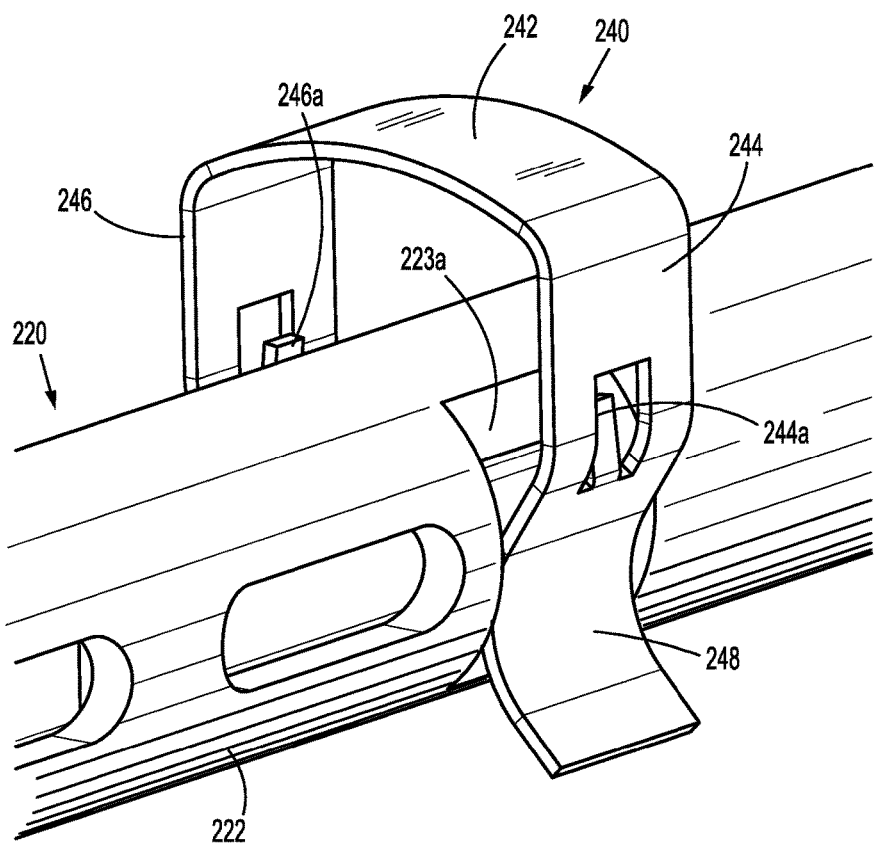
FIG. 14 is a front, perspective view of the removable trocar assembly and the retainer member of the locking mechanism shown in FIG. 14, engaged with one another.

With continued reference to FIG. 9, when the retainer member 140 is in a first or initial condition, the first and second locking posts 148, 150 thereof are separated by a first distance "$d_1$". When the retainer member 140 is moved to a second or flexed condition, as indicated by arrows "A", the first and second locking posts 148, 150 are separated by a second distance "$d_2$". As will be described in further detail below, the retainer remember 140 is in the first condition when the locking mechanism 130 is in the locked position (FIG. 7) and the retainer member 140 is in the second condition when the locking mechanism 130 is in the unlocked position (FIG. 10).

Each of the first and second locking posts 148, 150 of the retainer member 140 may include a tapered surface 148a, 150a, respectively. The tapered surfaces 148a, 150a facilitate movement of retainer member 140 to its second condition during receipt of the trocar assembly 120 within the throughbore 131 of the housing 132 of the locking mechanism 130. In this manner, the trocar assembly 120 may be received within the throughbore 131 of the housing 132 even when the locking mechanism 130 is in the locked position.

To effect movement of the retainer member 140 of the locking mechanism 130 from the first condition to the second condition, the housing 132 of the locking mechanism 130 includes a pair of ramps 134 (FIG. 6, shown in phantom, only one visible). The pair of ramps 134 extend outwardly from the housing 132 and are disposed adjacent the first and second openings 133a, 133b in the housing 132. The pair of ramps 134 are configured such that as the retainer member 140 is moved or pivoted from the locked position (FIG. 7) to the unlocked position (FIG. 10), the curved first and second leg portions 144, 146 of the retainer member 140 are flexed outwardly.

The pair of ramps 134 may also assist in maintaining the retainer member 140 in the locked position. In particular, when the retainer member 140 is in the locked position, engagement of the first and second leg portions 144, 146 of the retainer member 140 with the pair of ramps 134 frictionally prevents the retainer member 140 from pivoting to the open position without additional assistance from a clinician.

The operation of the locking mechanism 130 will now be described with reference to FIGS. 1-11, and specifically FIGS. 7-11. The adapter assembly 100 may be provided to the clinician with the trocar assembly 120 secured therein, or the trocar assembly 120 may be provided separate from the adapter assembly 100. If the trocar assembly 130 is provided to the clinician separately, prior to use, the trocar assembly 120 must be secured to the adapter assembly 100, wherein a proximal end of the trocar assembly 120 is inserted into and received through the throughbore 131 of the housing 132 of the locking mechanism 130. As noted above, tapered surfaces 148a, 150a of the first and second locking posts 148, 150, respectively, permit receipt of the trocar assembly 120 through the housing 132 when the retainer member 140 of the locking mechanism 130 is in the locked position. More particularly, when the retainer member 140 is in the locked position, engagement of the tapered surfaces 148a, 150a of the respective first and second locking posts 148, 150 by the trocar assembly 120 causes the first and second locking posts 148, 150 to flex outwardly to permit the trocar assembly 120 to be passed through the housing 132. When the trocar assembly 120 is fully seated within the adapter assembly 100, the retainer member 140 springs back to its initial condition (FIG. 8) to secure the trocar assembly 120 within the adapter assembly 100. When the trocar assembly 120 is fully seated within the adapter assembly 100, first and second locking posts 148, 150 engage and enter the respective first and second apertures 123a, 123b in the housing 122 of the trocar assembly 120. (see FIG. 8).

Alternatively, prior to insertion of the trocar assembly 120 through the throughbore 131 of the housing 132 of the locking mechanism 130, the retainer member 140 may be moved to the unlocked position to permit unobstructed receipt of the trocar assembly 120 through the housing 132. Once the trocar assembly 120 is fully seated with the adapter assembly 100, the clinician may move the retainer member 140 to the locked position to allow the retainer member 140 to return to the initial condition such that the first and second locking posts 148, 150 engage and enter the first and second apertures 123a, 123b in the housing 122 of the trocar assembly 120.

Subsequent to the trocar assembly 120 being secured within the adapter assembly 100, the adapter assembly 100 may be operated in a traditional manner.

With particular reference now to FIGS. 10 and 11, as discussed above, removal of the trocar assembly 120 from the adapter assembly 100 requires movement of the retainer member 140 of the locking mechanism 130 from the locked position (FIG. 8) to the unlocked position, as indicated by arrow "B" in FIG. 10. As the retainer member 140 is moved from the locked position to the unlocked position, the curved first and second leg portions 144, 146 are biased outwardly by the ramps 134 on the housing 132 of the locking mechanism 130 to move the respective first and second locking posts 148, 150 outwardly to the flexed condition. When the retainer member 140 is in the flexed position, the first and second locking posts 148, 150 of the retainer member 140 are completely withdrawn from within the first and second apertures 123a, 123b, respectively, of the housing 122 of the trocar assembly 120. In this manner, the trocar assembly 120 is no longer secured within the adapter assembly 100, and may be removed therefrom.

With reference now to FIGS. 12-16, an adapter assembly according to another embodiment of the present disclosure is shown generally as adapter assembly 200. The adapter assembly 200 is substantially similar to adapter assembly 100 described hereinabove, and will only be described further hereinbelow as relates to the differences therebetween.

The adapter assembly 200 includes a connector housing 208, a drive assembly 210 extending through the connector housing 208, and a locking mechanism 230 for releasably securing a trocar assembly 220 within the connector housing 208. The drive assembly 210 includes an inner flexible band assembly 212 and an outer flexible band assembly 214. The inner and outer flexible band assemblies 212, 214 are supported by upper and lower band guides 216, 218.

With continued reference to FIGS. 12-16, the locking mechanism 230 of the adapter assembly 200 includes a retainer member 240 for selective engagement with a housing 222 of the trocar assembly 220. The retaining member 240 is in the form of a flexible clip having a base portion 242, first and second leg portions 244, 246 extending from ends of the base portion 242, and first and second curved engagement portions 248, 250 extending from the respective first and second leg portions 244, 246. The first and second leg portions 244, 246 extend parallel to one another and are configured to be received about the upper band guide 216 (FIG. 15) of the drive assembly 210 of the adapter assembly 200. The engagement portions 248, 250 of the retainer member 240 curve radially inward towards one another and are configured to be selectively received within first and second retention slots 223a, 223b in a housing 222 of the trocar assembly 220. The first and second leg portions 244, 246 of the retainer member 240 are configured to flex outwardly to cause the respective engagement portions 248, 250 to move away from each other.

The retainer member 240 further includes a tab 244a, 246a extending inward from the first and second leg portions 244, 246, respectively. The tabs 244a, 246a engage the upper band guide 216 of the drive assembly 210 when the retainer member 240 is received over the upper band guide 216 to maintain the retainer member 240 about the upper band guide 216.

Figure 15:
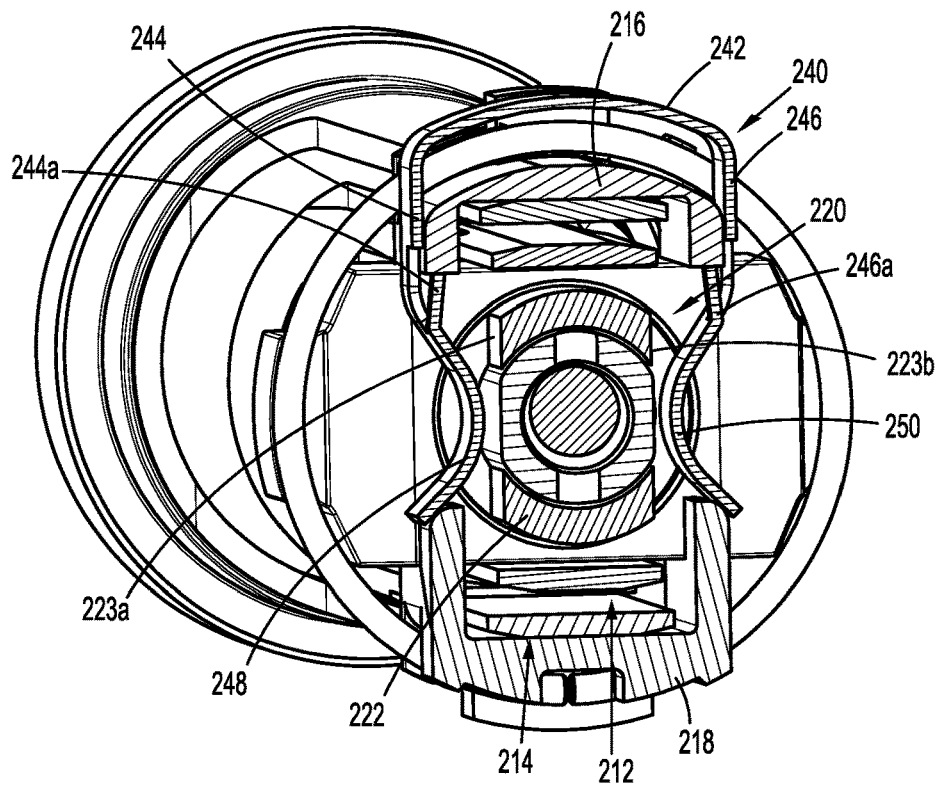
FIG. 15 is a cross-sectional perspective view taken along section line 15-15 shown in FIG. 12.

With particular reference now to FIG. 15, the locking mechanism 230 is shown with the retaining member 240 in a locked position. In the locked position, the base portion 242 and the first and second leg portions 244, 246 of the retainer member 240 are received about the upper band guide 216 of the drive assembly 210, and the first and second engagement portions 248, 250 of the retainer member 240 engage the lower band guide 218 of the drive assembly 210. Engagement of the first and second engagement portions 248, 250 with the lower band guide 218 biases the retainer member 240 radially outward. In this manner, the base portion 242 of the retainer member 240 is radially spaced from the upper band guide 216. As noted above, the tabs 244a, 246a of the retainer member 240 engage the upper band guide 216 to maintain the retainer member 240 about the upper band guide 216.

When the trocar assembly 220 is fully received within the adapter assembly 200, and the retainer member 240 is in the locked position, the engagement portions 248, 250 of the retainer member 240 are received within the first and second retention slots 223a, 223b of the trocar assembly 220. The engagement portions 248, 250 of the retainer member 240 secure the trocar member 240 within the adapter assembly 200.

Figure 16:
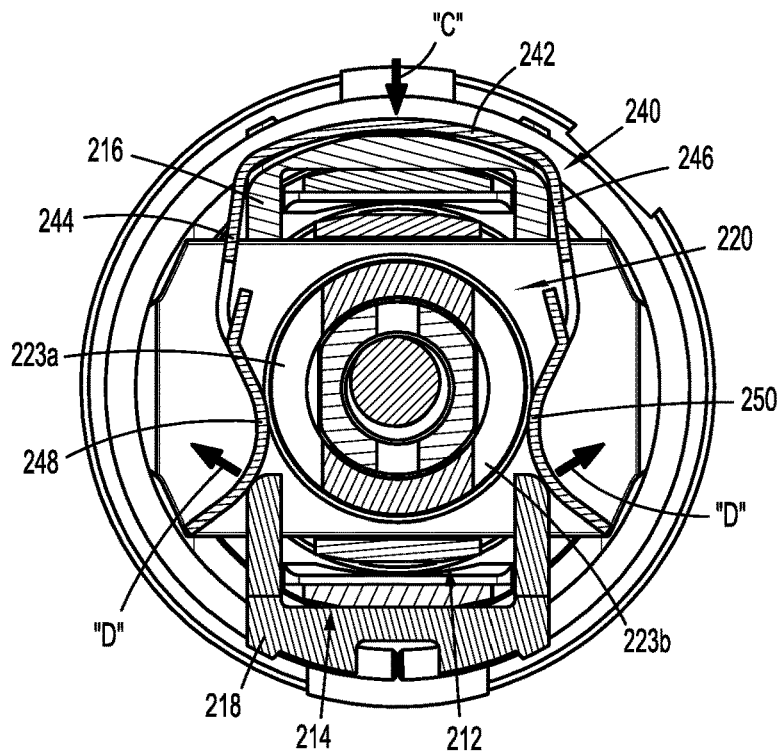
FIG. 16 is a cross-sectional end view taken along section line 15-15 shown in FIG. 12, with the locking mechanism thereof in an unlocked position.

With particular reference now to FIG. 16, the locking mechanism 230 is shown with the retainer member 240 in a second position. When the locking mechanism 230 is in the second position, the retainer member 240 is in a second or flexed condition. To move the retainer member 240 to the flexed condition, a clinician (not shown) depresses the base portion 242 of the retainer member 240, as indicated by arrow "C", to cause radially inward movement of the base portion 242 of the retainer member 240 with respect to the upper band guide 216.

As the retainer member 240 is moved radially inwardly, the first and second engagement portions 248, 250 of the retainer member 240 engage the lower band guide 218, causing the first and second leg portions 244, 246 and the first and second engagement portions 248, 250 to flex outwardly, as indicated by arrows "D" in FIG. 16. Movement of the first and second engagement portions 248, 250 to the flexed condition causes the first and second engagement portions 248, 250 to retract from within the respective first and second retention slots 223a, 223b of the housing 220 of the trocar assembly 220, thereby disengaging the retainer member 240 from the trocar assembly 220. Once the retainer member 240 is in the unlocked position, i.e., disengaged from the trocar assembly 220, the trocar assembly 220 may be removed from the adapter assembly 200.

Release of the retainer member 240 permits the retainer member 240 to return to the locked position (FIG. 15) due to the spring bias of the first and second engagement portions 248, 250 tending to urge the first and second engagement portions 248, 250 radially inward, and back into the first and second retention slots 223a, 223b of the trocar assembly 220, and thus move the base portion 242 radially outward. Loading of the trocar assembly 220 within the adapter assembly 200 may require the retainer member 240 to be moved to the unlocked position to permit the trocar assembly 220 to be received through the locking mechanism 230.

Figure 17:
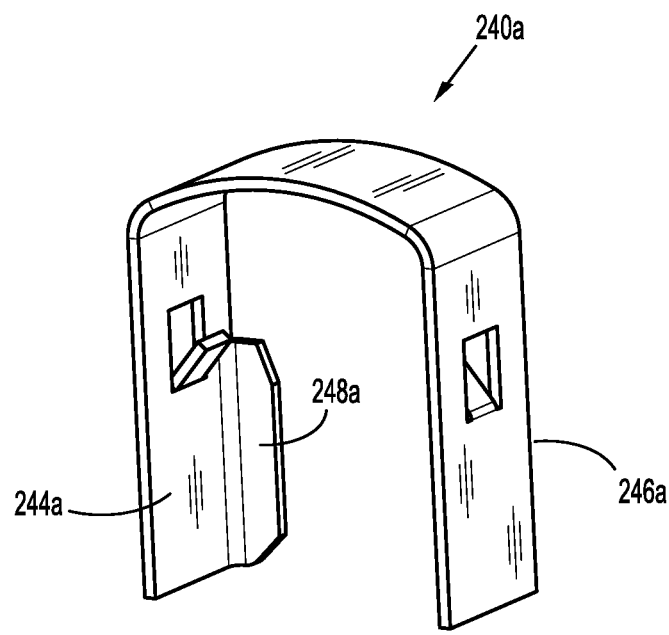
FIG. 17 is a perspective view of a retainer member according to an embodiment of the present disclosure.
Figure 18:
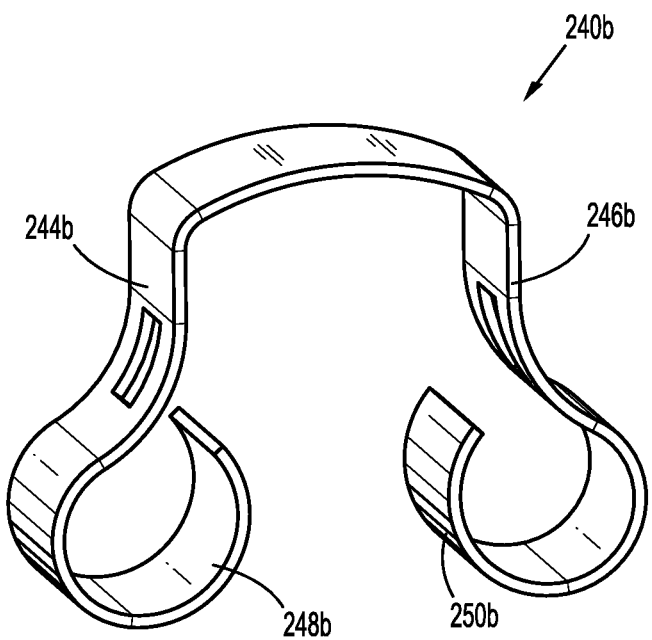
FIG. 18 is a perspective view of a retainer member according to another embodiment of the present disclosure.

With reference to FIGS. 17 and 18, alternative embodiments of a retainer member are shown generally as retainer members 240a (FIG. 17), 240b (FIG. 18). The retainer member 240a includes a pair of flanges 248a (only one shown) extending inwardly from respective first and second leg portions 244a, 246a. The flanges 248a, 250a are selectively receivable within first and second retention slots 223a, 223b (for example, see FIG. 16) of a trocar assembly 220 (for example, see FIG. 16) for releasably securing the trocar assembly within an adapter assembly 200 (for example, see FIG. 16). Similarly, the retainer member 240b includes a pair of curved engagement portions 248b, 250b extending from respective first and second leg portions 244b, 246b. The curved engagement portions 248b, 250b are selectively receivable within first and second retention slots 223a, 223b of a trocar assembly 220.

With reference now to FIGS. 19-24, an adapter assembly according to another embodiment of the present disclosure is shown generally as adapter assembly 300 (shown in phantom). The adapter assembly 300 is substantially similar to adapter assemblies 100, 200 described hereinabove, and will only be described as relates to the differences therebetween.

Figure 19:
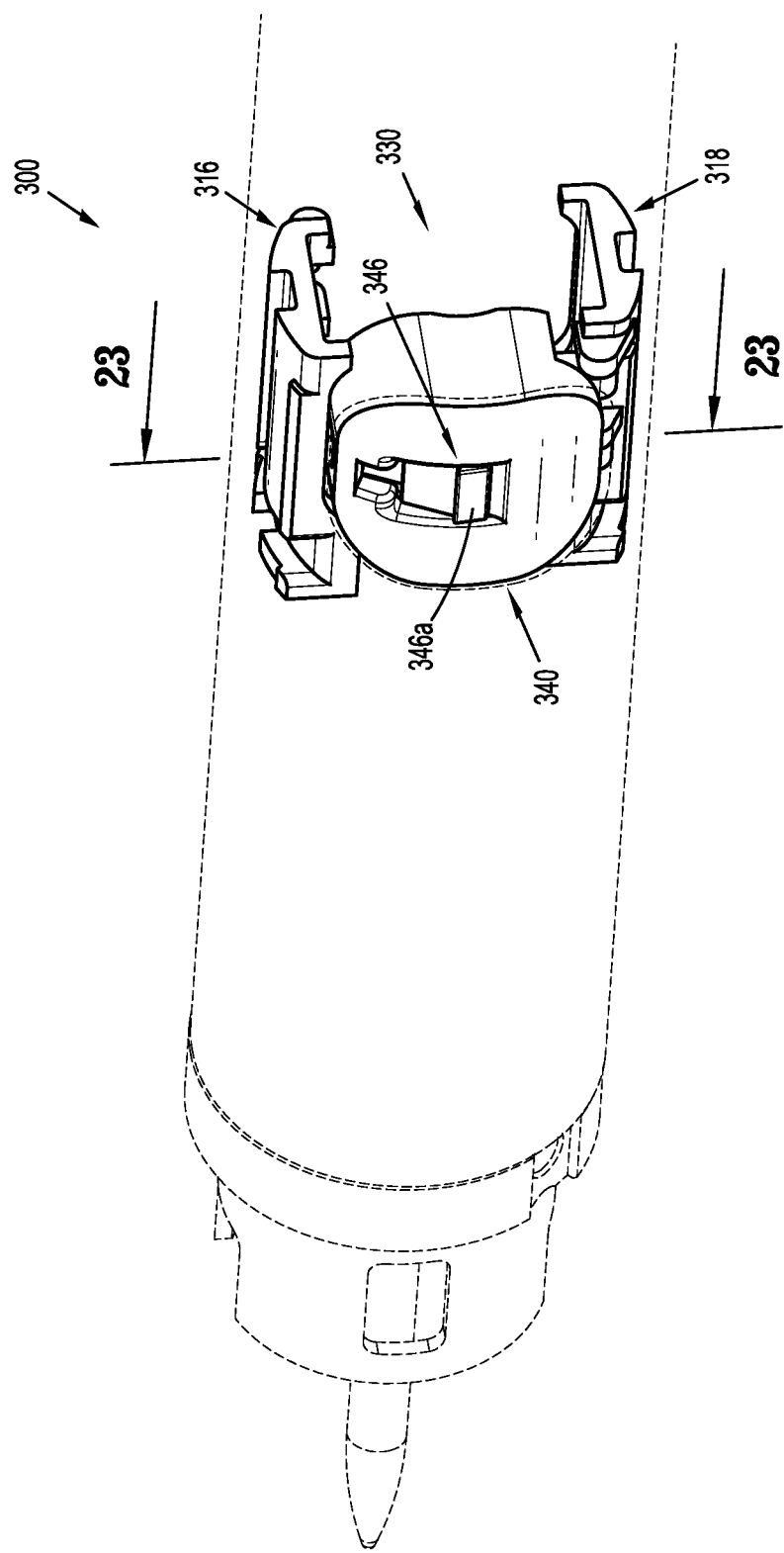
FIG. 19 is a rear, perspective side view of a distal end of an adapter assembly, according to a further embodiment of the present disclosure, shown in phantom, and including a locking mechanism and upper and lower band guides.
Figure 20:
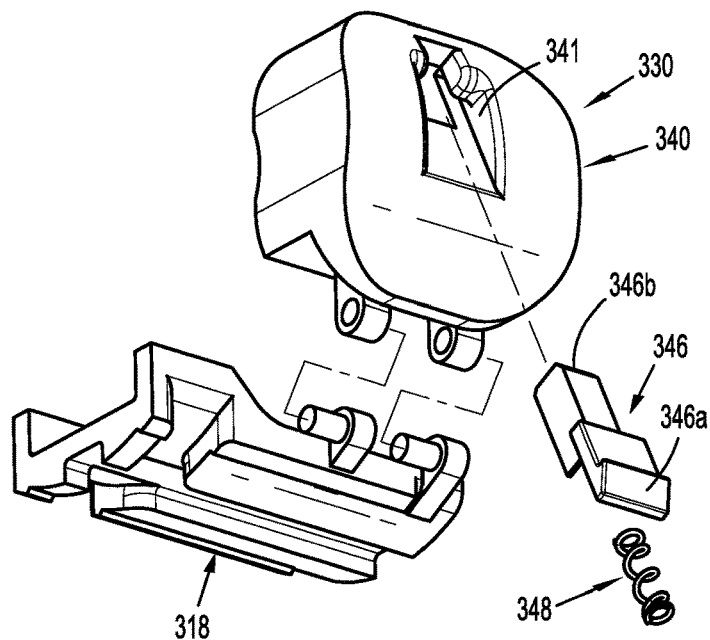
FIG. 20 is a perspective side view of the locking mechanism and the lower band guide shown in FIG. 19, with parts separated.
Figure 21:
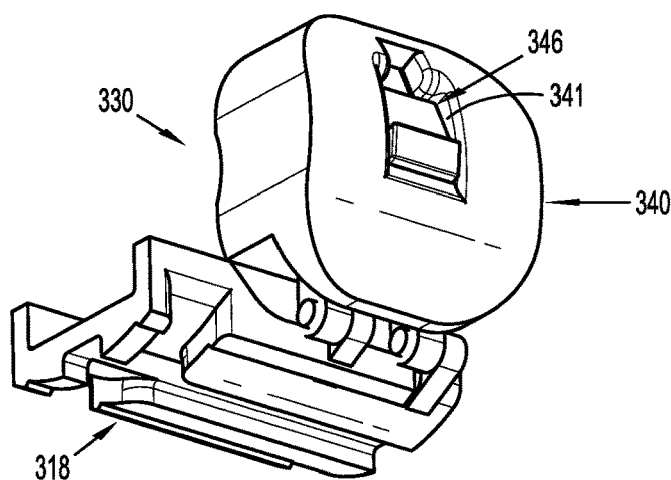
FIG. 21 is a perspective side view of the locking mechanism and the lower band guide shown in FIG. 19.
Figure 22:
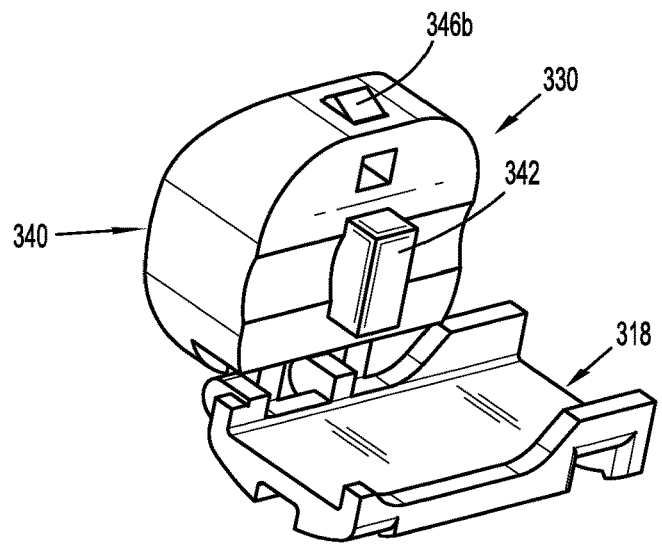
FIG. 22 is another perspective side view of the locking mechanism of the lower band guide shown in FIG. 19.
Figure 23:
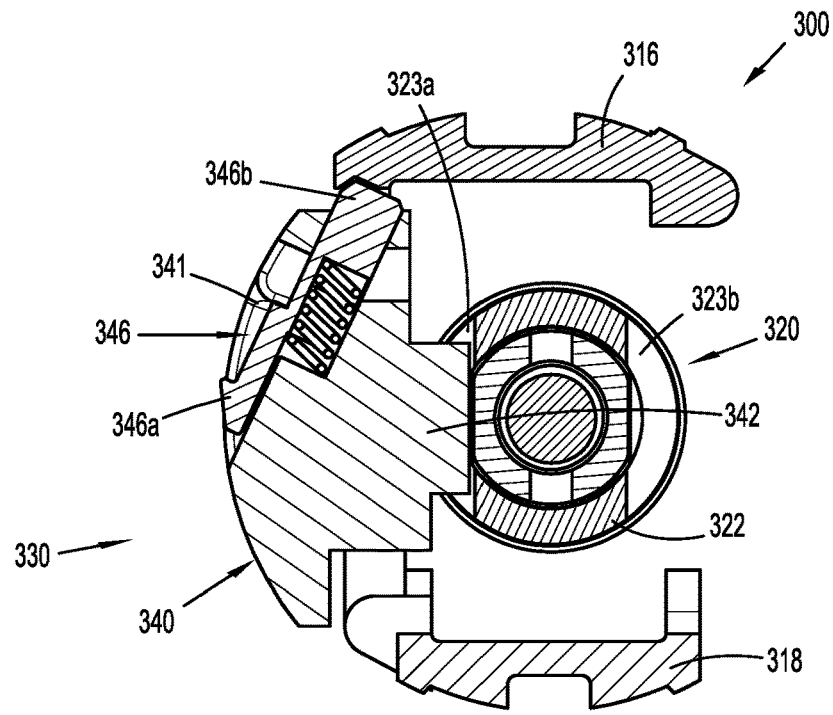
FIG. 23 is a cross-sectional end view taken along section line 23-23 shown in FIG. 19, with the locking mechanism in a locked position.

The adapter assembly 300 includes a locking mechanism 330 that operates to maintain a trocar assembly 320 within the adapter assembly 300 (FIG. 19). The locking mechanism 330 includes a retainer member 340 pivotally secured to a lower band guide 318 (FIGS. 23 and 24) of a drive assembly (not shown) of the adapter assembly 300 (FIG. 19), and a latch member 346 operably received within a cutout 341 of the retainer member 340. The retainer member 340 includes a protrusion 342 configured to be received within a first retention slot 323a of a housing 322 of the trocar assembly 320 when the locking mechanism 330 is in a locked position (FIG. 23). The latch member 346 includes an engagement portion 346a configured for operable engagement by a user, and a latch portion 346b configured to engage an upper band guide 316 of the drive assembly (not shown) of the adapter assembly 300. A biasing member, e.g., compression spring 338, biases the latch member 336 to a first position (FIG. 23).

Figure 24:
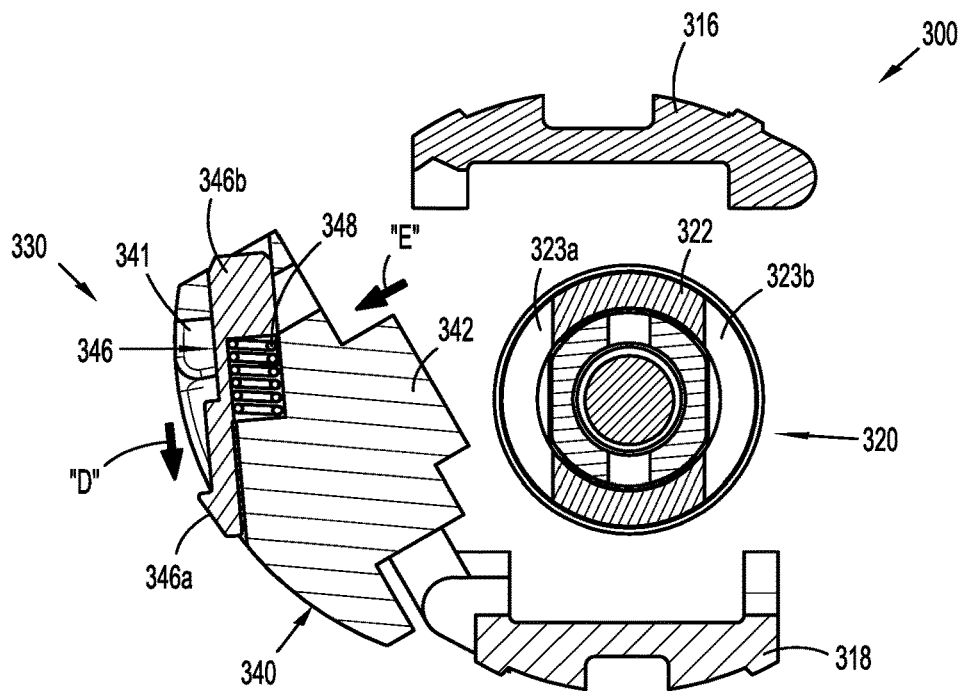
FIG. 24 is a cross-sectional end view taken along section line 23-23 shown in FIG. 19, with the locking mechanism in an unlocked position.

With particular reference to FIG. 24, the locking mechanism 330 is shown in the locked position. When the locking mechanism 330 is in the locked position, the protrusion 342 of the retainer member 340 is received within the first retention slot 323a of the housing 322 of the trocar assembly 320 and the lock portion 336b of the latch member 336 is engaged with the upper band guide 316 (FIGS. 23 and 24). Although shown only including a single retainer member 340, it is envisioned that the locking mechanism 340 may include a second retainer member (not shown) pivotally secured to the lower band guide 318 and including a protrusion (not shown) receivable within the second retention slot 323a of the housing 322 of the trocar assembly 320.

Turning now to FIG. 25, the locking mechanism 330 is shown in the unlocked position. To move the locking mechanism 330 to the unlocked position, the clinician presses downward against the engagement portion 346a of the latch member 346, as indicated by arrow "D", to move the lock portion 346b of the latch member 346 out of engagement with upper band guide 316. Once the lock portion 346b of the latch member 346 is disengaged from the upper band guide 316, the retainer member 340 may be pivoted to the unlocked position, as indicated by arrow "E", to remove the protrusion 342 of the retainer member 340 from within the first retention slot 323a of the trocar assembly 320. The trocar assembly 320 may then be removed from the adapter assembly 300.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. For example, in any of the embodiments discussed herein, the trocar assembly may form part of a circular surgical stapler that is wholly or partially disposable and such instruments may have a separate adapter or the adapter may be formed as part of the handle assembly. The stapling instrument can be manually operated, powered through an integral or separate motor, or form part of a robotic system.

What is claimed is:

1. An adapter assembly for connecting a surgical loading unit to a handle assembly, the adapter assembly comprising:
    a sleeve;
    a trocar assembly releasably securable within the sleeve, the trocar assembly including a trocar housing and a trocar member selectively extendable from the trocar housing, the trocar housing defining first and second locking slots and the trocar member including a distal end configured for releasable connection with an anvil assembly; and
    a locking mechanism configured to releasably secure the trocar assembly within the sleeve, the locking mechanism including a retaining member having first and second engagement portions configured for selective reception within the respective first and second locking slots of the trocar housing.

2. The adapter assembly of claim 1, wherein the retainer member is a formed wire and the first and second engagement portions include first and second locking posts movable between a first position engaged with the trocar assembly such that the trocar assembly is securely received within the sleeve, and a second position disengaged from the trocar assembly such that the trocar assembly is removable from within the sleeve.

3. The adapter assembly of claim 2, wherein the retainer member is configured to be pivoted between the first position and the second position.

4. The adapter assembly of claim 1, wherein the retainer member includes a base portion, and first and second leg portions extending from the base portion, the first and second engagement portions extend from the respective first and second leg portions.

5. The adapter assembly of claim 1, wherein the sleeve includes a proximal portion configured for releasable engagement with a handle assembly and a distal portion configured for releasable connection with a loading unit.

6. An adapter assembly for connecting a surgical loading unit to a handle assembly, the adapter assembly comprising:
a sleeve;
a trocar assembly releasably securable within the sleeve, the trocar assembly including a trocar housing and a trocar member selectively extendable from the trocar housing, the trocar housing defining first and second locking slots; and
a locking mechanism configured to releasably secure the trocar assembly within the sleeve, the locking mechanism including a retaining member, a lock housing, and first and second ramp members extending from the lock housing, the retaining member including first and second engagement portions configured for selective reception within the respective first and second locking slots of the trocar housing, wherein the retainer member is a formed wire and the first and second engagement portions include first and second locking posts pivotable between a first position engaged with the trocar assembly such that the trocar assembly is securely received within the sleeve, and a second position disengaged from the trocar assembly such that the trocar assembly is removable from within the sleeve, the first and second ramp members being configured to urge the first and second locking posts from an initial position in engagement with the trocar housing to a spaced apart position disengaged from the trocar housing as the retainer member is moved from the first position to the second position.

7. An adapter assembly for connecting a surgical loading unit to a handle assembly, the adapter assembly comprising:
a sleeve;
a trocar assembly releasably securable within the sleeve, the trocar assembly including a trocar housing and a trocar member selectively extendable from the trocar housing, the trocar housing defining first and second locking slots; and
a locking mechanism configured to releasably secure the trocar assembly within the sleeve, the locking mechanism including a retaining member, the retaining member including a base portion, first and second engagement portions configured for selective reception within the respective first and second locking slots of the trocar housing, and first and second leg portions extending from the base portion, the first and second engagement portions extend from the respective first and second leg portions; and
upper and lower band guides, wherein the retainer member is slidably received over the upper band guide and engages the lower band guide.

8. The adapter assembly of claim 7, wherein engagement of the retainer member with the lower band guide biases the retainer member radially outwardly.

9. The adapter assembly of claim 7, wherein the retainer member is movable relative to the upper and lower band guides from a first position in engagement with the trocar housing, to a second position disengaged from the trocar housing.

10. The adapter assembly of claim 7, wherein the base portion of the retainer member is configured to be moved radially inward relative to the sleeve.

11. The adapter assembly of claim 7, wherein the retainer member further includes first and second posts for maintaining the retainer member about the upper band guide.

12. The adapter assembly of claim 7, wherein the first and second engagement portions include first and second tabs for engaging the trocar housing of the trocar assembly.

13. The adapter assembly of claim 7, wherein the first and second engagement portions are curved towards one another and are configured to engage the trocar housing of the trocar assembly.

14. An adapter assembly for connecting a loading unit to a handle assembly, the adapter assembly comprising:
a sleeve;
upper and lower band guides disposed within the sleeve;
a trocar assembly releasably securable within the sleeve, the trocar assembly including a trocar housing defining at least a first retention slot; and
a locking mechanism configured to releasably secure the trocar assembly within the sleeve, the locking mechanism including a retaining member pivotally secured to the lower band guide and including a protrusion configured for selective reception within the at least first retention slot of the trocar housing.

15. The adapter assembly of claim 14, wherein the retainer member is movable between a first position engaged with the trocar housing and a second position disengaged from the trocar housing.

16. The adapter assembly of claim 15, wherein the locking mechanism includes a latch member having an engagement portion for facilitating movement of the latch member by a user.

17. The adapter assembly of claim 16, wherein the locking mechanism further includes a spring for biasing the latch member to a locked position.

18. The adapter assembly of claim 16, wherein the latch member includes a locking portion for engaging the upper band guide when the retainer member is in the first position.

19. An adapter assembly for connecting a surgical loading unit to a handle assembly, the adapter assembly comprising:
a sleeve including proximal and distal portions, the proximal portion being configured for releasable engagement with a handle assembly and the distal portion being configured for releasable connection with a loading unit;
a trocar assembly releasably securable within the distal portion the sleeve, the trocar assembly including a trocar housing defining first and second locking slots and a trocar member having a distal end, the distal end of the trocar member being configured for releasable connection with an anvil assembly; and
a locking mechanism configured to releasably secure the trocar assembly within the sleeve, the locking mechanism including a retaining member having first and second engagement portions configured for selective reception within the respective first and second locking slots of the trocar housing.

* * * * *